(12) United States Patent
Ganshorn

(10) Patent No.: US 6,422,094 B1
(45) Date of Patent: Jul. 23, 2002

(54) METHOD FOR DETERMINING THE FLOW RATE AND/OR THE MOLECULAR MASS OF LIQUID OR GASEOUS MEDIA

(76) Inventor: Peter Ganshorn, Goldgrund 3, 97702 Münnerstadt (DE)

( * ) Notice: Subject to any disclaimer, the term of this patent is extended or adjusted under 35 U.S.C. 154(b) by 0 days.

(21) Appl. No.: 09/519,655

(22) Filed: Mar. 6, 2000

(51) Int. Cl.$^7$ ................................................ G01F 1/66
(52) U.S. Cl. .................................................. 73/861.29
(58) Field of Search ...................... 73/861.27, 861.28, 73/861.29, 861.31

(56) References Cited

U.S. PATENT DOCUMENTS

| | | | | |
|---|---|---|---|---|
| 3,818,757 A | * | 6/1974 | Brown | 73/861.28 |
| 4,185,498 A | * | 1/1980 | Watson et al. | 73/861.27 |
| 4,515,021 A | * | 5/1985 | Wallance et al. | 73/861.27 |
| 5,753,824 A | * | 5/1998 | Fletcher-Haynes | 73/861.28 |

* cited by examiner

*Primary Examiner*—Max Noori
(74) *Attorney, Agent, or Firm*—Edwin D. Schindler

(57) ABSTRACT

Method for determining the flow rate and/or the molecular mass of liquid or gaseous media in flow measuring instruments, especially pneumotachographs, with the aid of the measurement of the transit time of ultrasonic pulses in the medium between two ultrasonic transmitters/receivers, especially piezoelectric transmitters/receivers, where an ultrasonic impulse is emitted from a transmitter (1), and simultaneously the run of a time duration starts which is slightly shorter than the transit time in the static medium, after the end of the time duration the discharge of a capacitor, to which a voltage is applied, commences with a constant current intensity, the discharge is terminated with the registration of the ultrasonic pulse in the receiver (2), the voltage still applied to the capacitor is measured and the discharge time is determined, the transit time from the time duration and the discharge is added up, the measurement of the transit time is repeated in the opposite direction, and the flow rate and/or the molecular mass is determined from the different transit times.

7 Claims, 2 Drawing Sheets

Figure 1:
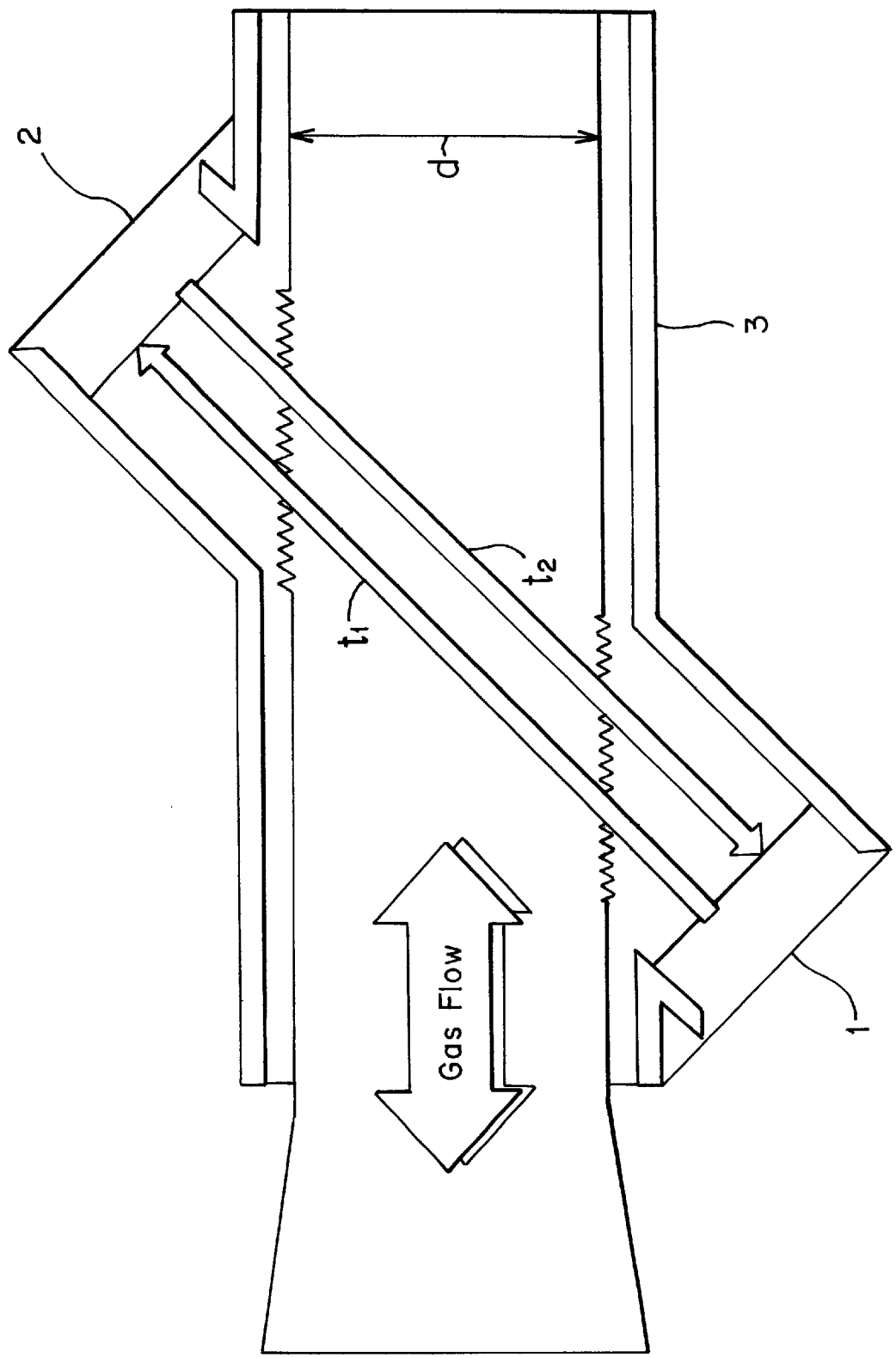

METHOD FOR DETERMINING THE FLOW RATE AND/OR THE MOLECULAR MASS OF LIQUID OR GASEOUS MEDIA

BACKGROUND OF THE INVENTION

1. Technical Field of the Invention

The invention concerns a method for determining the flow rate and/or the molecular mass of liquid or gaseous media in flow measuring instruments, especially pneumotachographs, with the aid of the measurement of the transit time of ultrasonic pulses in the medium between two ultrasonic transmitters/receivers, especially piezoelectric transmitters/receivers, as well as a flow measuring instrument for executing the method.

2. Description of the Prior Art

The determination of the flow rate and molecular mass of gaseous media is of interested in industry as well as in medicine, e.g. when recording various lung function parameters such as tidal volume or gas exchange in the lung. To that end, measuring instruments are known, which function with different physical principles. In the case of ultrasonic transit time methods, the change in the speed of propagation of sound waves in relation to the moving medium is used in order to determine of the flow rate and/or the molecular mass. An ultrasonic pulse is transmitted essentially in the direction of movement through the medium whose transit time is measured over the defined distance between the transmitter and the receiver, and the procedure is repeated immediately thereafter in the opposite direction. Thereby, the speed of propagation of the pulse through the flow of the medium is increased or lowered, and from the different values, the flow rate or the molecular mass can be determined. The method can also be applied to liquid media. The physical principles and the formulae for calculating the desired values can be taken from the articles 'Technologie der Ultraschall-Spirometrie' by C. Buess, W. Guggenbühl and K. Hamoncourt in the journal 'Atemwegsund Lungenkrankenheiten', $21^{st}$ year, no. September 1995, pp 438–442, and 'Die Molmasse der Atemluft' by T. Kenner and K. Harnoncourt, ibid, pp 454–456, with the bibliographical references specified there. In medicine engineering, pneumotachographs, which use this measuring principle, are known and in use, whereby either the time between emittance and reception are measured directly electronically, i.e. counted by a clocked counter, or if a transmitter transmits ultrasonic waves continuously, the phase displacement is determined in the receiver. The required measures are known to a person skilled in the art. Standard pneumotachographs have flow pipes with a diameter of 2–3 cm so that the transmitters/receiver have a mutual spacing of approx. 5 cm, and this returns transit times of some 150 microseconds. The flow rate that occurs during normal breathing of 1 m/s results in a change of the transit time in the magnitude of one microsecond, as can be calculated using the above mentioned formulae. Moreover, the composition of expired air, which contains approx. 5% $CO_2$ by volume compared with the inspired air, changes the transit time in this magnitude. As ultrasonic transmitters/receivers, preferably piezoelectric quartz resonators are used with a resonance frequency of several 100 kHz, as can be taken from the state-of-the-art. They offer the advantage of high frequency stability, and a short settling time so that the temporal interval between the reception and transmission of a pulse by a quartz resonator is very short, and during this period the flow conditions in the flow pipe hardly change and corrupt the measuring result. With the simultaneous emittance of pulses from both transmitters, the measurements would be corrupted through overlay of reflected sound waves.

A disadvantage of the methods known until now for determining the transit time consists in the type of transit time measurement. As described above, the time changes only by a few microseconds so that the actual measurement is only relevant in a short time segment around the value of the transit time in the standing medium. In order to resolve one microsecond with sufficient accuracy, it should be divided at least into 1.000 time intervals, that is, effect a measurement in the nanosecond range. The clocked counters used to count the time between transmission and reception of the signal function with frequencies in the GHz range. Because, however, the total transit time is counted, a relative error of, for example, only 1% results already in corruptions that lie in the magnitude of the transit time change. A more accurate time resolution, i.e. a faster counter, is moreover hardly realisable.

SUMMARY OF THE INVENTION

The invention has the object of measuring the transit time of an ultrasonic pulse in a moved medium with sufficient accuracy.

This task is solved according to the invention therein that an ultrasonic pulse is emitted from a transmitter, and simultaneously the run of a time duration starts, which is slightly shorter than the transit time in the static medium, after the end of the time duration the discharge of a capacitor, to which a voltage is applied, commences with a constant intensity of current, the discharge is terminated with the registration of the ultrasonic pulse in the receiver, the voltage still applied to the capacitor is measured and the discharge time is determined, the transit time from the time duration and the discharge is added up, the measurement of the transit time is repeated in the opposite direction, the flow rate and/or the molecular mass is determined from the different transit times.

The central idea of the invention relates to the concept that the actual time measurement commences only briefly before the probable arrival of the ultrasonic pulse in the receiver, and the charge stored in a capacitor is used for the time measurement. As explained above, the transit time is subject to only minor changes so that the actual measurement does not have to be started until briefly before the end of the known transit time in the static medium. It can be determined with a dry run, i.e. without flow, and then a slightly shorter time duration be set, e.g. 148 instead of 150 microseconds with a transit time change of approx. 1 microsecond, as the so-called dead time, upon expiry of which the discharge of a capacitor is commenced. Through application of a voltage, the capacitor is charged with a known charge. It is possible for the person skilled in the art to discharge the current with a constant intensity so that the charge stored in the capacitor and thus the voltage is reduced continuously. With the registration of the pulse in the receiver, the discharge process is then terminated. The voltage applied to the capacitor is converted into the discharge duration of the capacitor, according to the formula t=(C×U): I, where the capacitor capacity is C, the voltage U and the constant discharge current I. It is added to the dead time and the total transit time of the ultrasonic pulse from the transmitter to the receiver obtained. After the process has been repeated immediately subsequently in the opposite direction, i.e. the previous receiver acts as a transmitter and vice versa, the transit times of the ultrasonic pulse are measured with the direction of movement and against the direction of movement, and with the known formulae the flow rate and the molecular mass of the medium can be calculated. The measures required, i.e. the coupling of a receiver to a capacitor, and the determination of the discharge time and the addition to the dead time and the calculation of the desired measuring result, can be effected automatically through electronic circuits, as is known for the trained person skilled in the art.

The advantage of the invention consists therein that the measurement of electrical quantities, such as the voltage applied to the capacitor in mV, can be executed with cost-effective measuring instruments and insignificant measuring errors. Furthermore, the analog output signals can be processed with known electric circuits, e.g. operational amplifiers, so that the evaluation of the measuring results, i.e. the summation and subtraction of the transit times, is realisable in a simple way. Moreover, by means of the shorter time duration, during which the measurement is executed, there is a reduction in the absolute magnitude of the relative measuring error, which occurs with every measurement, because an error of 1% in the case of a microsecond corrupts the result less as in the case of the measuring methods described above. This method can be used in the broadest range of fields, also industrial and commercial. For instance, it is possible to measure the intake rate of air in a combustion engine, or the flow of fuel in a line.

Advantageous embodiments of the method and an instrument to execute the method are the object of subclaims.

To adapt the method to the broadest range of gaseous or liquid media, an advantageous embodiment consists therein to change the time duration and/or the voltage applied to the capacitor and/or the discharge voltage. Because in different media the ultrasonic pulses have different sound velocities, the time duration which expires prior to the commencement of the measurement is adjusted. With a change in the voltage applied to the capacitor and in the discharge current, an adjustment to the required measuring range is achieved. If, for example, the capacitor current is increased, with a constant discharge current, a longer time duration can be measured, as is necessary with a faster flow and a related large change in the transit time. Likewise, it is possible simultaneously to increase the discharge current so that the reduction, e.g. by one mV, in the capacitor current is always assigned to the same time period in order to obtain a constantly high resolution of the respective measuring range.

A simplification of the method consists therein to determine the transit time of a pulse in the static medium, and to adjust the voltage applied to the capacitor and/or the discharge current so that the voltage 0V, which is reached after a particular discharge duration, is assigned to the transit time in the static medium, i.e. that the zero crossing of the capacitor current, when a positive voltage has been applied, corresponds to the instant at which a pulse in the static medium would have been registered in the receiver. Thereby the measuring range, i.e. the voltage and the discharge current intensity, are adjusted to the respective medium with its flow rate. The advantage consists therein that with a linear approach, as described further below, the small changes in the transit time, or the measured applied voltage, upon termination of the discharge, are directly convertible with the aid of known circuits into the change of the flow rate or the molecular mass, whereby the transit times each deviate by the same small value from the time in the static medium.

In a simplification of the calculation of the flow rate and/or the molecular mass of the medium, it is assumed that a small change of the flow rate is proportional to a small change in the transit time, or conversely proportional to the change in the molecular mass. With the formula for calculating the flow rate, this linearisation is presented exemplarily: it contains the term $(t_1-t_2)/(t_1*t_2)$, with the two different transit times which each differ by the small amount d from transit time $t^0$ in the static medium. This yields: $((t_0+d)-(t_0-d))/(t_0^2-d^2)=(2*d)/t_0^2$. Because $d^2$ is small in the second order, it is negligible how an estimation of the magnitudes obtains: $t_0$ in the sample embodiment of the drawing is 150 microseconds and d approximately one microsecond so that there is a relative error of 0.005%. It follows that the small change in the flow rate is proportional to the small transit time change d. This approximation of course applies to only a limited range, which is to be determined for each medium and each flow rate, i.e. so long the deviation from the actual value is smaller than the measuring error of the device. The advantage of linearisation consists therein that the voltages measured at the capacitor in mV can be converted directly into the change of the flow rate or the molecular mass, which can be executed easily with the aid of known circuits.

A possible method for determining the molecular mass concerns therein to effect the determination in the static medium. This has the consequence that the transit times of the ultrasonic pulses, which are transmitted in the opposite direction through the medium, have the same amount. Here it is irrelevant according to the invention how the medium is brought to a quiescent condition in the flow pipe in relation to the pipe.

The apparative design of a flow measuring instrument, which is based on the novel measuring method, is similar to that of a known flow measuring instrument, as used in medicine or measurement techniques in the broadest range of the fields. The ultrasonic transmitters/receivers here are piezoelectric quartz resonators, which are directly coupled to a capacitor to determine the discharge time. The implementation of corresponding control electronics, which start the discharge process and stop it upon reception of the ultrasonic pulse and according to one of the methods described above determine the transit time, is possible for a person skilled in the art. The advantage with such an instrument consists therein that the new method can be performed with existing instruments, and only the control and evaluation electronics on the quartz resonators are modified, whereby the signals are available in analog form and can be converted in a known way into the flow rate or the molecular mass, e.g. with the aid of operational amplifiers.

BRIEF DESCRIPTION OF THE DRAWING FIGURES

Figure 2:
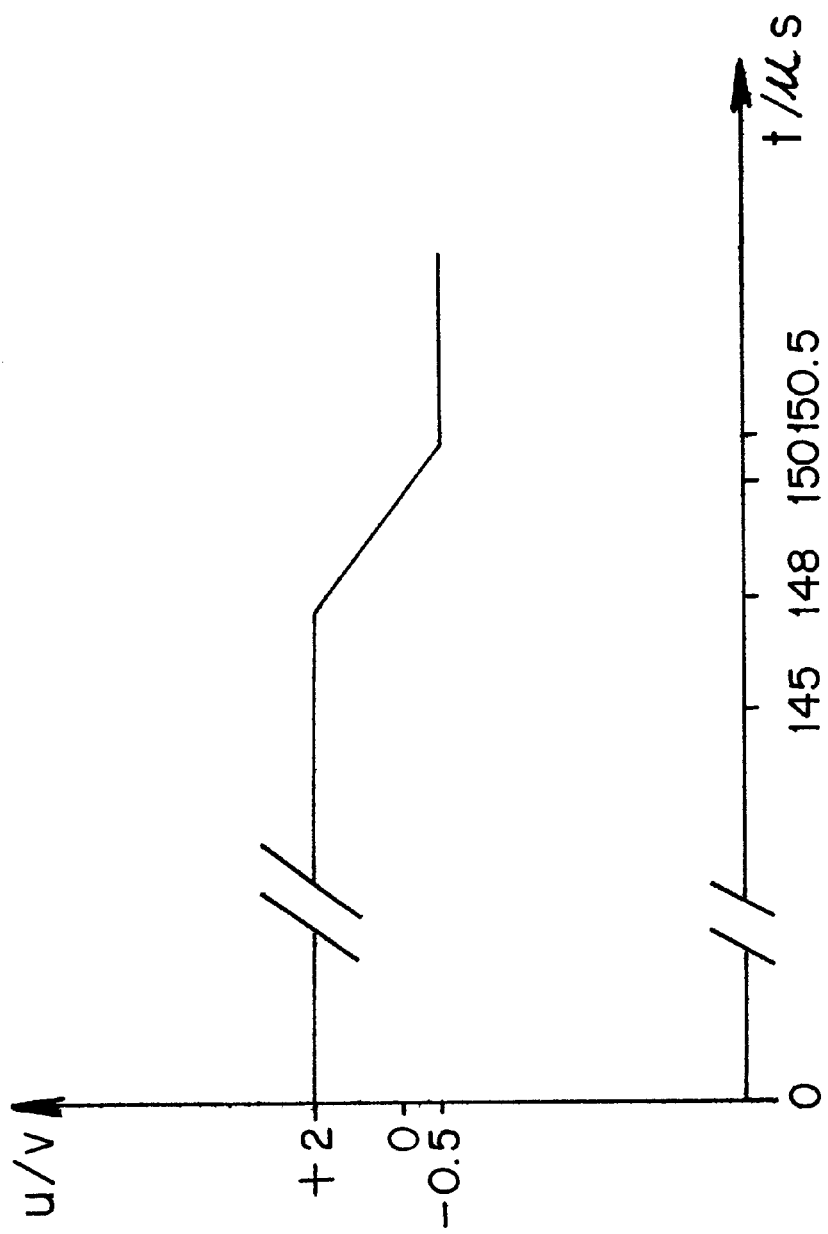

Further details, features and advantages of the invention can be taken from the following description part in which with the aid of drawings a typical embodiment of the invention is explained in greater detail. It shows:

FIG. 1 the schematic design of a pneumotachograph,

FIG. 2 the time characteristic of a voltage applied to a capacitor.

DETAILED DESCRIPTION OF THE DRAWING AND PREFERRED EMBODIMENTS

The diameter of the flow pipe (3) is normally approximately 2–3 cm so that the transmitters/receivers (1,2) are at a distance of some 5 cm to each other and with the sound velocity in air of approximately 331 m/s the transit time of 150 microseconds is obtained in the static medium. In case of medical pneumography, the air flows with a rate of 1 m/s with regular respiration alternately in both directions through pipe (3), as shown by the arrow. The design is essentially the same as with the known pneumotachographs, only that with this method the transmitters/receivers (1, 2) are provided with capacitors and special control electronics.

The diagram shown in FIG. 2 concerns the discharge curve of the capacitor, whereby the absciss is calibrated in volts and the ordinate in microseconds. At instance t=0, i.e. when an ultrasonic pulses is emitted in the transmitter, a previously defined time duration commences, in this example 148 microseconds. It is determined with a dry run in the static medium and then several microseconds are deducted from this time in order to execute a measurement around this value in only a limited time window. Upon its expiry, the discharge of a capacitor commences, which in this example was charged with an applied voltage of +2V, with a constant current intensity. The control electronics required to that end are known to a person skilled in the art. The receiver connected to the capacitor so that the received pulse of the ultrasonic signal, in this example after 150.5 microseconds, terminates the discharge of the capacitor at a value of 0.5 V. From this current and the known discharge current intensity, the discharge duration can be calculated in a simple way. This is added by the electronic circuit to the time duration and the transit time obtained in this way calculated. After an ultrasonic pulse has been emitted in the opposite direction, the second transit time is calculated. From these two values, in a known way, the flow rate or the molecular mass of the moving gas can be calculated.

What is claimed is:

1. A method for determining a flow rate or molecular mass of a liquid media or a gaseous media, comprising the steps of:

emitting an ultrasonic pulse in a first direction from a transmitter in a flowable media;

running a time duration which is slightly shorter than a known transit time of said ultrasonic pulse in a static medium of said flowable media, said step of emitting said ultrasonic pulse and said step of running said time duration commencing simultaneously;

discharging a capacitor, to which a voltage is applied, commencing with a constant current intensity in said flowable media, said step of discharging said capacitor commences after ending of said time duration;

terminating said discharging of said capacitor, when said ultrasonic pulse is registered in a receiver for receiving said ultrasonic pulse, while continuing to apply voltage to said capacitor;

determining a discharge time by measuring said voltage still being applied to said capacitor;

determining a first-direction transit time by adding together said time duration and said discharge time;

determining a second-direction transit time by adding together said time duration and said discharge time in a second direction, said time duration and said discharge time in said second direction being determined by repeating said steps for determining said first-direction transmit time, said second direction being an opposite direction of flow of said flowable media from said first direction; and, calculating said a flow rate or molecular mass of a liquid media or a gaseous media from a difference between said first-direction transit time and said second-direction transit time.

2. The method for determining a flow rate or molecular mass of a liquid media or a gaseous media according to claim 1, wherein said time duration is variable.

3. The method for determining a flow rate or molecular mass of a liquid media or a gaseous media according to claim 1, wherein said voltage applied to said capacitor is variable.

4. The method for determining a flow rate or molecular mass of a liquid media or a gaseous media according to claim 1, wherein current for discharging said capacitor is variable.

5. The method for determining a flow rate or molecular mass of a liquid media or a gaseous media according to claim 1, wherein voltage 0V applied to said capacitor is assigned to said known transit time of said ultrasonic pulse in said static medium.

6. The method for determining a flow rate or molecular mass of a liquid media or a gaseous media according to claim 1, wherein said calculating said molecular mass of a liquid media or a gaseous media is carried out in said static medium.

7. The method for determining a flow rate or molecular mass of a liquid media or a gaseous media according to claim 1, wherein said transmitter is a piezoelectric transmitter and said receiver is a piezoelectric receiver.

* * * * *